United States Patent
Takarada

(10) Patent No.: US 7,356,165 B2
(45) Date of Patent: Apr. 8, 2008

(54) IMAGING APPARATUS PERFORMING A HIGH RELIABILITY DATA ANALYSIS

(75) Inventor: Shinichi Takarada, Niihama (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 571 days.

(21) Appl. No.: 11/073,711

(22) Filed: Mar. 8, 2005

(65) Prior Publication Data

US 2005/0201600 A1 Sep. 15, 2005

(30) Foreign Application Priority Data

Mar. 9, 2004 (JP) ............................. 2004-065184

(51) Int. Cl.
*G06K 9/00* (2006.01)
(52) U.S. Cl. ..................................... 382/103
(58) Field of Classification Search ................ None
See application file for complete search history.

(56) References Cited

U.S. PATENT DOCUMENTS 5,506,912 A * 4/1996 Nagasaki et al. ........... 382/103
5,857,059 A * 1/1999 Yamagishi .................. 386/125
6,922,478 B1 * 7/2005 Konen et al. ............... 382/115

FOREIGN PATENT DOCUMENTS

JP 5-130545 5/1993

* cited by examiner

*Primary Examiner*—Matthew C. Bella
*Assistant Examiner*—Alex Liew
(74) *Attorney, Agent, or Firm*—Wenderoth, Lind & Ponack, L.L.P.

(57) ABSTRACT

Provided is an imaging apparatus which can detect an occurrence of a vibration using imaged images without a new constituent such as a vibration sensor being added thereto, wherein when imaging a position reference image for checking positions of observation targets on the image and a plurality of luminance reference images for checking the spectral distributions of the observation targets, a first vibration detection unit detects a vibration for the position reference image, a mask image for checking the positions is created on the basis of the position reference image for which no vibration is detected, and the luminance reference image is compared with the mask image every time the luminance reference image is imaged, thereby to judge whether positions deviate or not, and in a case where the positions deviate, the position reference image is re-imaged, thereby eliminating the image imaged with a vibration occurring.

9 Claims, 13 Drawing Sheets

IMAGING APPARATUS PERFORMING A HIGH RELIABILITY DATA ANALYSIS

FIELD OF THE INVENTION

The present invention relates to an imaging apparatus that stores acquired and processed images as well as analyzes the same. More particularly, the present invention relates to an imaging apparatus which eliminates vibrating components from the target images and performs a high reliability data analysis.

BACKGROUND OF THE INVENTION

In recent years, an image processing technique using an imaging apparatus is applied in various fields, and there are many applications to such as a gene expression analyzer in medical fields. For example, there is a gene expression analyzer using a real time PCR method, a DNA micro array (also referred to as DNA chip), or a semiconductor nanocrystal.

A description will be given hereinafter of a gene expression analyzer using a fluorescence microscope as a prior art imaging apparatus.

Imaging targets by the prior art gene expression analyzer are beads having various spectral characteristics, each having a diameter of about 10 μm. A specific mRNA is combined with a bead having each spectral characteristic. The gene expression analyzer images beads and analyzes the spectral characteristics of each beads, and thereby identifies an mRNA that corresponds to the kind of the existing beads.

FIG. 13 is a block diagram illustrating a prior art gene expression analyzer using a fluorescence microscope.

In the prior art gene expression analyzer 600 shown in FIG. 13, there are provided a well plate 601 comprising a plurality of wells 602 for receiving a plurality of beads as observation targets, a well plate driving unit 603 for moving the well plate 601 in X and Y directions on a two-dimensional plane, a position reference imaging unit 630 for imaging silhouettes of the plurality of beads, a luminance reference imaging unit 640 for imaging luminance images of plural beads through plural optical filters each having a passing wavelength and different from each other, a CCD camera controller 611 for controlling a CCD camera 610, and a CPU 620 which analyzes the images imaged by respective imaging units 630 and 640 as well as controls the whole apparatus 600.

More specifically, the position reference imaging unit 630 includes an LED 606 as reference light, an objective lens 605, a z-axis driving unit 612 for moving the objective lens 605 in z-axis direction, a dichroic mirror 607 for reflecting a light of wavelength less than a predetermined value while passing a light of wavelength equal to or larger than the predetermined value, an imaging lens 609, and a CCD camera 610. A LED light from the LED 606 is applied to the plural beads as observation targets in the well 602, and the obtained silhouette lights of the beads are enlarged by the objective lens 605 to pass through the dichroic mirror 607 and the bandpass filter 608, and are collected by the imaging lens 609. Then, the z-axis driving unit 612 drives the objective lens 605 to align the focus position of the objective lens 605, and the CCD camera 610 images the silhouette lights to output a silhouette image as a two-dimensional image.

The luminance reference imaging unit 640 includes an excitation light source 613, an objective lens 605, a z-axis driving unit 612, a dichroic mirror 607, a filter wheel 614 which holds plural bandpass filters 608 each passing only a predetermined wavelength band, a filter wheel driving unit 615 which rotatably drives the filter wheel 614, an imaging lens 609, and a CCD camera 610. An excitation light from the excitation light source 613 is reflected by the dichroic mirror 607 and is applied to the plural beads as observation targets in the well 602 passing through the objective lens 605. The light generated in accordance with the spectral characteristic of the respective beads in response to the applied light are enlarged by the objective lens 605, and passes through the dichroic mirror 607 and the bandpass filter 608 to be collected by the imaging lens 609. Meanwhile, the z-axis driving unit 612 drives the objective lens 605 so as to align the objective lens 605 in its focus position, and then the CCD camera 610 images the light which is emitted from the respective beads and is collected by the imaging lens 609, to obtain a luminance image as a two-dimensional image.

Further, the CPU 620 includes a controller 621 which controls the whole apparatus 600, an analysis unit 622 which analyzes the two-dimensional image imaged by the CCD camera 610, and a mask image creation unit 623 which creates mask image that shows the existing area of the beads as imaging targets on the basis of the position reference image.

An operation of the prior art gene expression analyzer will be described. FIG. 14 is a flowchart illustrating a series of operations for obtaining the spectral characteristics of beads as observation targets in the prior art gene expression analyzer.

Initially, in step S101, position reference images for obtaining existing positions of plural beads as imaging targets are captured into the CPU 620 in the apparatus 600. To be specific, the controller 621 in the CPU 620 controls the well plate driving unit 603 so as to move the well plate 601 receiving the observation targets to be positioned right above the objective lens 605. Then, the controller 621 makes the LED 606 light to apply the LED light to the well 602. The LED light becomes the silhouette light for the beads as observation targets in the well 602, and the silhouette light is enlarged by the objective lens 605 and passes through the dichroic mirror 607 and the bandpass filter 608 to be collected by the imaging lens 609, and then reaches the CCD camera 610. The controller 621 instructs the z-axis driving unit 612 to align the objective lens 605 in its focus position so as to image the silhouette lights, and then instructs the CCD camera controller 611 to make the CCD camera 610 image the silhouette images of the plural beads as observation targets. Then, the analysis unit 622 in the CPU 620 binarizes the imaged silhouette images, and the binarized images are stored in the CPU 620 as position reference image for obtaining existing positions of the respective targets.

In step S102, a plurality of images which have passed through the respective optical filters are captured into the CPU 620 as images for obtaining luminance values of the respective imaging targets. To be specific, the controller 621 initially makes the LED 606 unlighted and makes the excitation light source 613 apply an excitation light. The excitation light is a light of short wavelength such as a blue laser beam. When the excitation light is incident on the dichroic mirror 607, due to the characteristic of the dichroic mirror 607 that it reflects a light of wavelength less than a predetermined value, the dichroic mirror 607 reflects the excitation light in the direction toward the objective lens 605. The objective lens 605 focuses the light from the dichromic mirror 607 on the observation targets in the well 602. The plural beads as observation targets existing in the well 602 present light emission patterns which respectively correspond to the spectral characteristics of the respective beads in response to the light applied from the objective lens 605, and the lights emitted from the respective beads pass through the objective lens 605, the dichroic mirror 607, and the bandpass filter 608, and further are collected by the imaging lens 609, and then reach the CCD camera 610 similarly as described above for the silhouette lights. At this time, since the bandpass filter 608 only passes a specific wavelength band, only the light of the specific wavelength band among the light emitted from the observation targets reaches the CCD camera 610. The controller 621 instructs the CCD camera controller 611 to make the CCD camera 610 image luminance images of only the specific wavelength bands having passed through the bandpass filter 608 among the light emitted from the observation targets. Then, the analysis unit 622 in the CPU 620 binarizes the imaged luminance images to be stored in the CPU 620 as luminance reference images.

In step S103, it is confirmed whether a predetermined number of luminance reference images obtained as above are captured or not, and when it does not yet reach the predetermined number, the controller 621 controls the filter wheel driving unit 615 to rotate the filter wheel 614 and to set the bandpass filter 608 passing a different wavelength band in the light path. Then, after performing the same processing as described above, the CCD camera 610 images a luminance image of a specific wavelength band which has passed through the newly set bandpass filter 608 among the light emitted from the observation targets. The analysis unit 622 then binarizes the imaged luminance image to be stored in the CPU 620 as a new luminance reference image. This processing is repeated a predetermined number of times until for example eight pieces of luminance reference images are obtained, and luminance reference images of various wavelengths are obtained.

After obtaining the position reference image and the luminance reference images as above, the processing transits to an analysis step of identifying the kind of the plural beads as observation targets using those reference image.

Here, the beads appearing on the respective luminance reference images and the beads appearing on the position reference image should be located at the same positions. Accordingly, in the analysis step, the respective luminance values of the respective beads are obtained for each optical filter from the respective luminance reference images, to identify the kind of the beads is identified on the basis of the luminance values.

Initially, in step S104, the mask image creation unit 623 in the CPU 620 creates a mask image indicating the bead presence areas using the captured position reference image.

FIG. 15 is a diagram illustrating a mask image and luminance reference images. In FIG. 15, reference numeral 801 denotes a mask image showing bead presence areas, which is obtained by performing a masking processing that masks higher luminance portions at the center portions of the beads in the position reference image.

In FIG. 15, reference numeral 701a denotes a first luminance reference image obtained after passing through the bandpass filter 608 that passes a light of 505 nm wavelength, the reference numeral 701b denotes a second luminance reference image obtained after passing through the bandpass filter that passes a light of 525 nm wavelength, and the reference numeral 701c denotes a third luminance reference image obtained after passing through the bandpass filter that passes a light of 545 nm wavelength.

Here, 8 pieces of bandpass filters 608 that respectively passes the lights having wavelengths different from each other by 20 nm are used to obtain 8 pieces of luminance reference images in total.

FIG. 15 shows only first three pieces among 8 pieces of luminance reference images.

The areas B1$m$, B2$m$, and B3$m$ on the mask image 801 are bead presence areas where the beads B1, B2, and B3 are present, respectively, and the areas B1$a$ to B1$c$, the areas (B2$a$ to B2$c$) (do not appear in FIG. 15), and the areas B3$a$ to B3$c$ on the first to third luminance reference images 701$a$ to 701$c$ are areas on the luminance reference images which correspond to the areas B1$m$, B2$m$, and B3$m$ on the mask image 801, respectively.

In steps S105 to S106, assuming that the positions of the bead areas B1$a$ to B1$c$, B2$a$ to B2$c$, and B3$a$ to B3$c$ which are present on the respective luminance reference images are the same as the positions of the bead area B1$m$, B2$m$, and B3$m$ which are present on the mask image 801, respectively, the analysis unit 622 in the CPU 620 obtains the respective luminance average values of the areas B1$a$ to B1$c$, B2$a$ to B2$c$, and B3$a$ to B3$c$ on the respective luminance reference images.

Assuming, for example, that a luminance average value of the area B1$a$ on the first luminance reference image 701$a$ is A, a luminance average value of the area B1$b$ on the second luminance reference image 701$b$ is B, and a luminance average value of the area B1$c$ on the third luminance reference image 701$c$ is C, in step S107, the luminance average values obtained as above are plotted to result in FIG. 16.

FIG. 16 is a diagram illustrating the plotted luminance average values of the respective areas on the luminance reference images, which areas correspond to the three bead areas on the mask image.

In FIG. 16, the abscissas indicates a wavelength transmitting through the bandpass filter while the ordinates indicates the luminance average value. The reference numeral 901 indicates a spectral curve indicating the characteristic of beads B1, obtained by plotting the 8 luminance average values of the areas on the first to eighth luminance reference images corresponding to the bead presence area B1$m$ and connecting the plot points. Reference numeral 902 indicates a spectral curve indicating the characteristic of beads B2, obtained by plotting the respective luminance average values of the areas on the luminance reference images corresponding to the bead presence area B2$m$ and connecting the plot points. Reference numeral 903 indicates a spectral curve indicating the characteristic of beads B3, obtained by plotting the respective luminance average values of the areas on the luminance reference images corresponding to the bead presence area B3$m$ and connecting the plot points.

In step S108, the analysis unit 622 analyzes the spectral characteristics of the respective beads B1 to B3 on the basis of the respective spectral curves 901 to 903 thus obtained and identifies the kinds of the beads, respectively.

In the conventional method, as shown in FIG. 17(a), assuming that, when the mask image is overlaid on the first luminance reference image, the bead areas B1$m$ to B3$m$ on the mask image and the bead areas B1$a$ to B3$a$ on the first luminance reference image are located at the same positions, respectively, luminance average values of the respective areas on the luminance reference images corresponding to the bead presence areas B1$m$ to B3$m$ on the mask image are obtained and the kinds of the beads are respectively identified on the basis of the average values.

In this conventional method, however, there is no means for detecting vibrations, and even when vibrations occur while the luminance reference image is being imaged and thereby the position of the beads on the luminance reference image is changed, the processing is performed similarly as described above. Therefore, when the mask image is overlay-displayed on the luminance reference image and a deviation has occurred between the beads presence areas B1m to B3m on the mask image and the bead areas on the luminance reference images as shown in FIG. 17(b), the analysis unit 622 cannot obtain luminance average values of the respective beads on the respective luminance reference images correctly, and thereby the kinds of the beads cannot be properly identified.

FIGS. 17(a) and 17(b) are diagrams illustrating relationships between the beads areas present in the mask image and the bead areas present in the first luminance reference image, wherein FIG. 17(a) shows a case where the mask image is overlaid on the luminance reference image in its display when no vibrations occur and FIG. 17(b) shows a case where the mask image is overlaid on the luminance reference image in its display when vibrations occur.

To solve this problem, it may be conceived to mount a vibration detection sensor close to the imaging target and to judge whether the positions of the beads has deviated or not before or during imaging the respective luminance reference images employing the technique disclosed in the Japanese Published Patent Application No. Hei.5-130545.

However, when the vibration detection method as disclosed in the above patent reference is employed, it is necessary to provide a vibration sensor in the apparatus 600, which results in an increase in cost as well as necessitating a large amount of labor for interrelating the vibrations and the deviations in the beads positions.

This comes from that as long as a detailed analysis is not made as to the amplitude and the direction of the vibrations, a mounting position of a sensor, and relationships between the vibrations and the sensor positions, it is difficult to properly relate the allowable range for the sensor output and the allowable range for the actual beads position deviations.

SUMMARY OF THE INVENTION

The present invention is directed to solving the above described problems and has for its object to provide an imaging apparatus that can detect an occurrence of vibrations, and can perform data analysis with high accuracy, without providing a new constituent such as a vibration sensor in the apparatus.

Other objects and advantages of the invention will become apparent from the detailed description that follows. The detailed description and specific embodiments described are provided only for illustration since various additions and modifications within the spirit and scope of the invention will be apparent to those of skill in the art from the detailed description.

In order to solve the above-described problems, according to a 1st aspect of the present invention, there is provided an imaging apparatus which comprises: a position reference image creation unit for applying reference light to plural imaging targets each having the same shape, and creating silhouettes of the imaging targets, thereby to obtain a position reference image utilized for obtaining positions at which the respective imaging targets are present; a luminance reference image creation unit for applying an excitation light to the imaging targets, and creating luminance images of the imaging targets for respective optical filters each having a predetermined passing wavelength band, thereby to obtain plural luminance reference images utilized for obtaining luminance of respective imaging targets for each optical filter; a first vibration detection unit for detecting at least one among a change amount of the number or the area and a shape change of the imaging targets on the position reference image, and judging whether vibrations have occurred in the respective imaging targets during imaging the imaging target by the position reference image creation unit on the basis of the detected result; a mask image creation unit for creating a mask image that shows areas where the imaging targets are present from the position reference image for which the first vibration detection unit has detected no vibrations; and a second vibration detection unit for overlay-displaying the mask image on the respective luminance reference images, detecting whether or not the imaging targets are present outside the existing areas of the respective imaging targets, and judging whether or not vibrations have occurred in the respective imaging targets during imaging the imaging target by the luminance reference image creation unit on the basis of the detected result.

Therefore, it can be detected whether or not a vibration occurred during imaging using an image obtained by the apparatus.

According to a 2nd aspect of the present invention, in the imaging apparatus of the 1st aspect, the first vibration detection unit includes a shape change detection unit for obtaining a characteristic amount indicating a shape change of each imaging target in the position reference image, the characteristic amount detected by the first vibration detection unit is compared with a predetermined threshold value for the characteristic amount, and when among the plural imaging targets in the position reference image, there are present a predetermined number of or a predetermined rate of imaging targets that have the characteristic amounts larger than the threshold value, it is judged that vibrations have occurred.

Therefore, it can be detected whether or not a vibration occurred when the silhouettes of the imaging targets were imaged using the obtained position reference image.

According to a 3rd aspect of the present invention, in the imaging apparatus of the 2nd aspect, the characteristic amount for the imaging target having a spherical shape is the largest diameter of the imaging target.

Therefore, a shape of the imaging target can be easily obtained.

According to a 4th aspect of the present invention, in the imaging apparatus of the 2nd aspect, the characteristic amount for the imaging target that has a spherical shape and comprises a substance of a high light transparency is the largest diameter of a high luminance portion of the imaging target.

Therefore, a shape of the imaging target can be more properly and easily obtained.

According to a 5th aspect of the present invention, in the imaging apparatus of the 1st aspect, the mask image creation unit creates a mask image by pasting areas corresponding to the imaging targets and their outer circumference areas in the position reference image for which imaging target areas no vibrations are detected by the first vibration detection unit.

Therefore, it can be easily detected whether or not a vibration occurred before or when the luminance image of the imaging target was imaged using the created mask image.

According to a 6th aspect of the present invention, in the imaging apparatus of the 1st aspect, the second vibration detection unit overlay-displays the mask image on the luminance reference images, and compares the luminance values of the pixels that are located outside the existing areas of the imaging targets in the luminance reference images with a predetermined threshold value for the luminance value, and when among the pixels located outside the existing areas of the imaging targets, there are present a predetermined number of or a predetermined rate of pixels that have the luminance values larger than the threshold value, it is judged that vibrations have occurred.

Therefore, it can be more reliably detected whether or not a vibration occurred during imaging using the mask image.

According to a 7th aspect of the present invention, in the imaging apparatus of the 1st aspect, the second vibration detection unit overlay-displays the mask image on the luminance reference images, and compares the luminance values of the pixels that are located close to the outer circumferences of the existing areas of the imaging targets in the luminance reference images with a predetermined threshold value for the luminance value, and when among the pixels that are located close to the circumferences of the existing areas of the imaging targets, there are present a predetermined number of or a predetermined rate of pixels having higher luminance values than the threshold value, it is judged that vibrations have occurred.

Therefore, it can be detected in a shorter time whether or not a vibration occurred before or when a luminance image was imaged since the targets to be detected are reduced.

According to an 8th aspect of the present invention, in the imaging apparatus of the 1st aspect, when vibrations are detected by either the first vibration detection unit or the second vibration detection unit, all of the position reference image and the respective luminance reference images are newly captured.

Therefore, an image for which a vibration is detected can be securely eliminated, and as a result reliability of the data analyzed by the apparatus can be substantially improved.

According to a 9th aspect of the present invention, in the imaging apparatus of the 1st aspect, when vibrations are detected by either the first vibration detection unit or the second vibration detection unit, the luminance reference images for which vibrations are detected as well as the position reference image for obtaining the existing positions of the imaging targets on the luminance reference images for which vibrations are detected are newly captured.

Therefore, a time for eliminating the images for which a vibration is detected and obtaining all the images can be shortened.

BRIEF DESCRIPTION OF THE DRAWINGS

FIG. 3 shows an image obtained when no vibration occurred while the position reference image imaging unit was performing imaging according to the first embodiment of the present invention wherein

FIG. 4 shows an image obtained when a strong vibration occurred while the position reference image imaging unit was performing imaging according to the first embodiment of the present invention wherein

FIG. 5 shows an image obtained when a gentle vibration occurred while the position reference image imaging unit was performing imaging according to the first embodiment of the present invention wherein

FIG. 7 is a diagram for explaining a method for creating a mask image according to the first embodiment of the present invention wherein

FIG. 9 is a diagram illustrating a relationship between a mask image and a first luminance reference image according to the first embodiment of the present invention, wherein

FIG. 17 is a diagram illustrating a relationship between a mask image and a first luminance reference image for the prior art wherein

DETAILED DESCRIPTION OF THE PREFERRED EMBODIMENT

Hereinafter, embodiments of an imaging apparatus according to the present invention will be described in detail with reference to the drawings.

[Embodiment 1]

The imaging apparatus according a first embodiment detects whether or not a vibration occurs before or while an image is imaged on the basis of the imaged images. Here, in the first embodiment, a gene expression analyzer which analyzes spectral characteristics of beads which are present in the imaged image and identifies the kinds of the beads, thereby identifying mRNAs corresponding to the kinds of the beads, respectively, is taken as an example of an imaging apparatus as described in the background of the invention.

Further, imaging targets are beads having various spectral characteristics, each of which has a diameter of about 10 μm.

Figure 1:
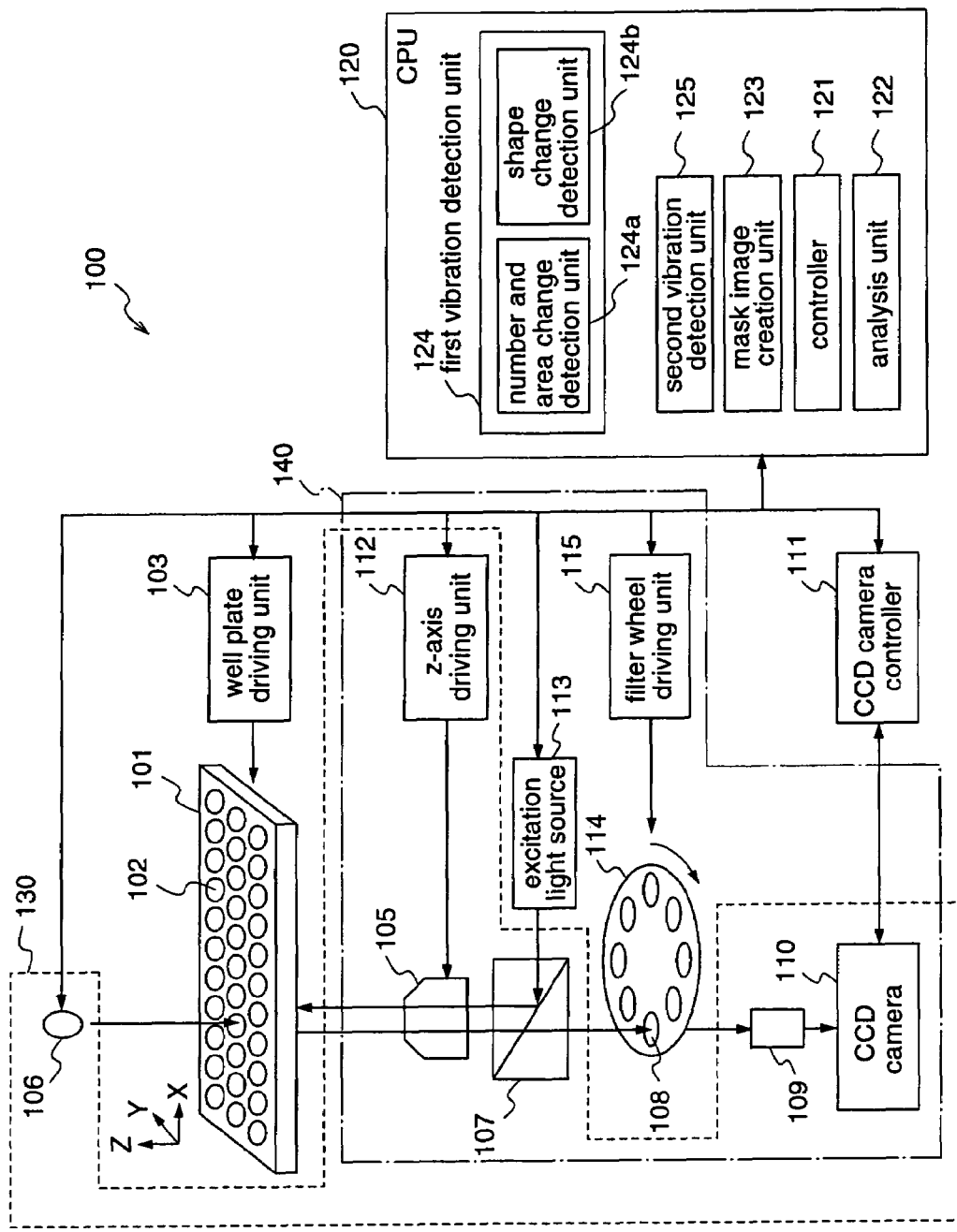
FIG. 1 is a diagram illustrating a construction of a gene expression analyzer using a fluorescence microscope according to the present invention.

FIG. 1 is a diagram illustrating a construction of the gene expression analyzer according to the first embodiment.

In FIG. 1, the gene expression analyzer 100 according to the first embodiment comprises: a well plate 101 formed by a plurality of wells 102 into which a plurality of beads as observation targets are injected; a well plate driving unit 103 which moves the well plate 101 in the X and Y directions on the two-dimensional plane; a position reference image imaging unit 130 which images silhouettes of the plurality of beads as imaging targets; a luminance reference image imaging unit 140 which images luminance images of the beads through a plurality of optical filters each having a passing wavelength band different from each other, respectively; a CCD camera controller 111 which controls a CCD camera 110; and a CPU 120. The CPU 120 is provided with a first vibration detection unit 124 which detects whether or not a vibration occurred when the position reference image was being imaged and a second vibration detection unit 125 which detects whether or not a vibration occurred before or when the luminance reference image was imaged in addition to a controller 121 which controls the whole apparatus 100, an analysis unit 122 which analyzes images imaged by the CCD camera 110, and a mask image creation unit 123 which creates a mask image indicating bead presence areas on the basis of the position reference image.

Figure 11:
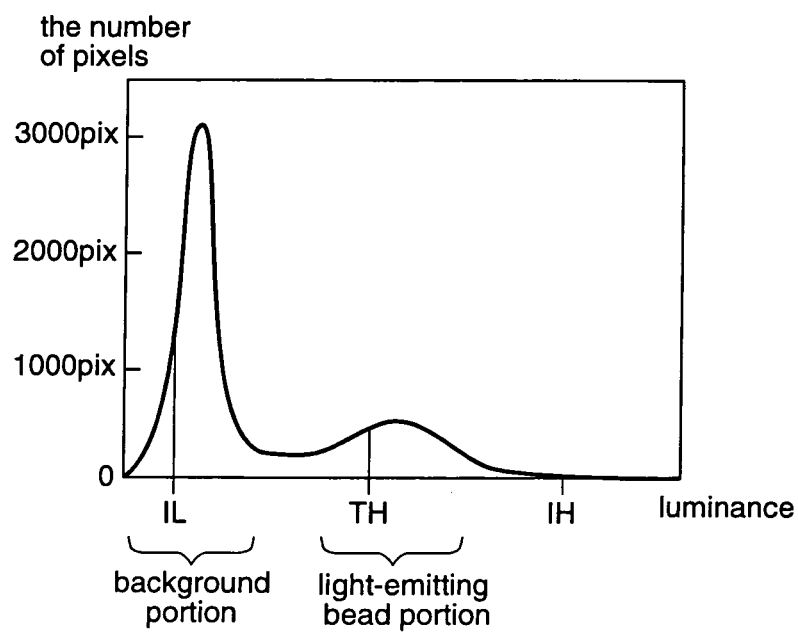
FIG. 11 shows a histogram which is created on the basis of a first luminance reference image according to the first embodiment of the present invention.

Then, in FIG. 1, the portions identical or corresponding to those shown for the prior art apparatus 600 in FIG. 11 are denoted by the reference numerals identical or corresponding to those designated for the prior art apparatus.

Hereinafter, a description will be given in detail. The position reference image imaging unit 130 in the apparatus 100 includes a LED 106 as reference light, an objective lens 105, a z-axis driving unit 112; a dichroic mirror 107; an imaging lens 109, and a CCD camera 110. A LED light from the LED 106 is applied to the plurality of beads as observation targets in the well 102, and the obtained silhouette lights of the beads are enlarged by the objective lens 105 and then pass through the dichroic mirror 107 and the bandpass filter 108, and are collected by the imaging lens 109. At this time, the objective lens 105 is aligned with the focus position by means of the z-axis driving unit 112, and the CCD camera 110 images the silhouette lights to obtain a silhouette image which is transformed into a two-dimensional image.

The luminance reference image imaging unit 140 in the apparatus 100 includes an excitation light source 113, an objective lens 105, a z-axis driving unit 112, a dichroic mirror 107, a filter wheel 114, a filter wheel driving unit 115, an imaging lens 109, and a CCD camera 110. An excitation light from the excitation light source 113 is applied to the plurality of beads as observation targets in the well 102 through the dichroic mirror 107 and the objective lens 105, and the lights emitted from the respective beads by the applied light are enlarged by the objective lens 105, and pass through the dichroic mirror 107 and the bandpass filter 108 and are collected by the imaging lens 109. At this time, the z-axis driving unit 112 moves the objective lens 105 to align the objective lens 105 with the focus position, and thereafter the CCD camera 110 images the lights emitted from the respective beads, which lights are collected by the imaging lens 109, to obtain a luminance image which is transformed into a two-dimensional image.

Next, an operation will be described.

Figure 14:
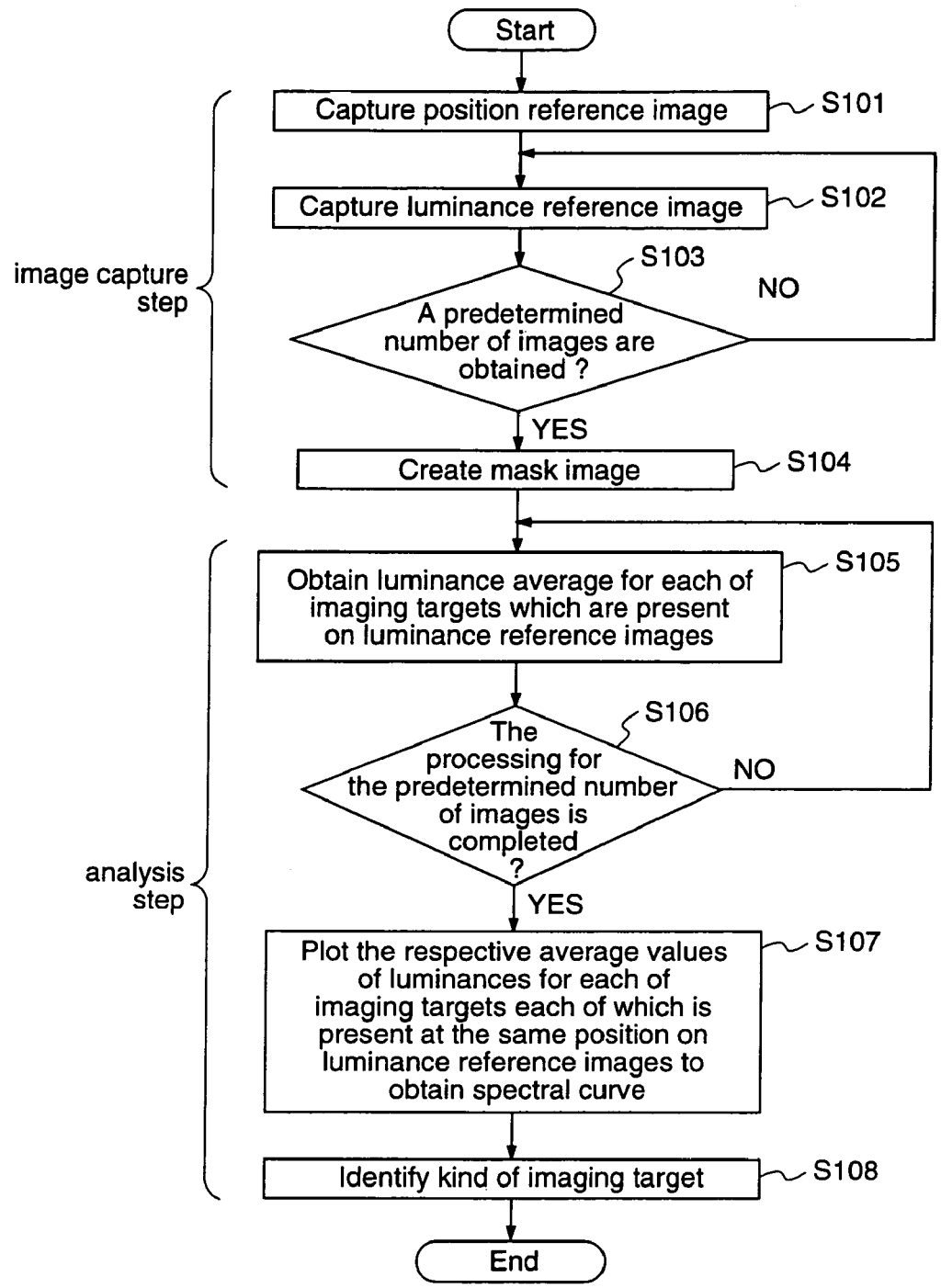
FIG. 14 is a flow chart illustrating a series of operations performed by the prior art gene expression analyzer.
Figure 15:
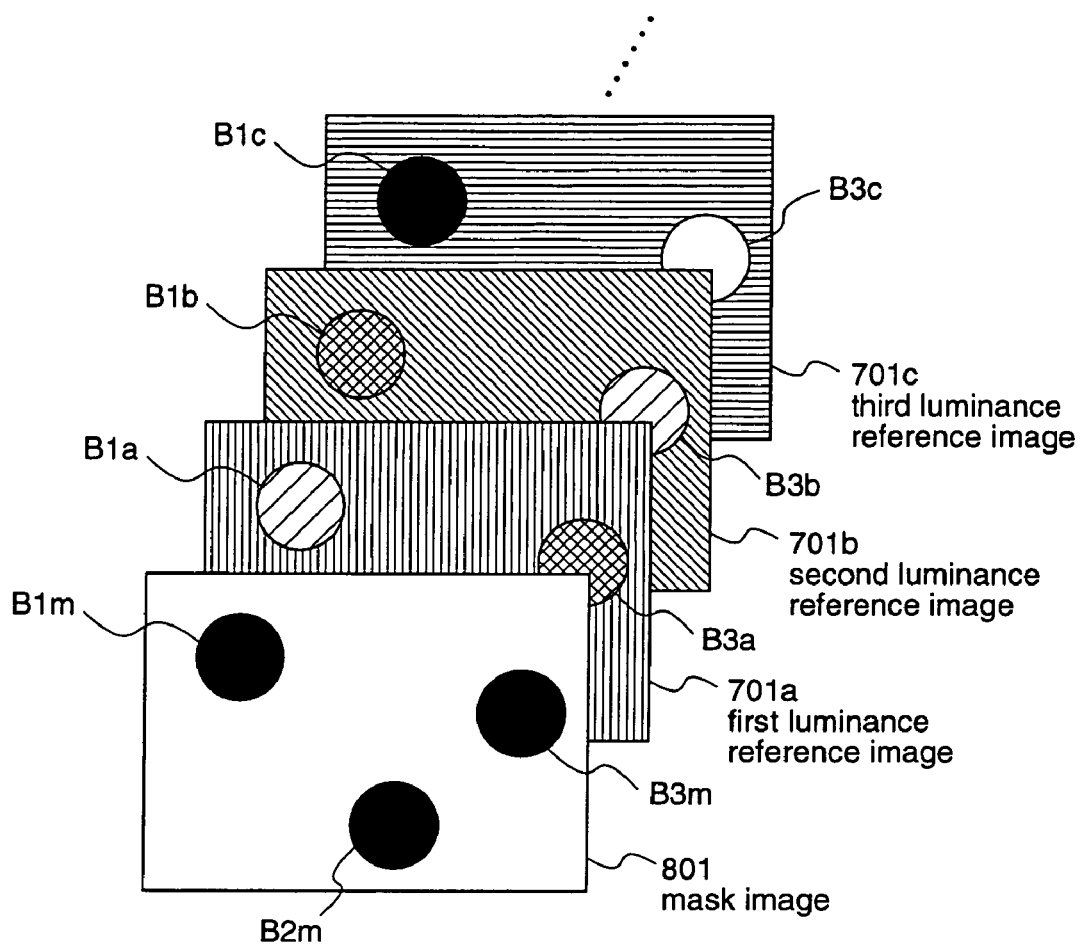
FIG. 15 is a diagram illustrating a mask image and a plurality of luminance reference images for the prior art.

The gene expression analyzer 100 according to the first embodiment images the plurality of beads as observation targets and captures a position reference image and a plurality of luminance reference images and then analyzes the spectral characteristics of the beads using the captured images as described above for the prior art apparatus 600 (refer to FIG. 14).

The process of the analysis steps according to the first embodiment is the same as the process of the analysis steps for the prior art apparatus, and here a process of image capture steps of capturing images will be described in detail.

Figure 2:
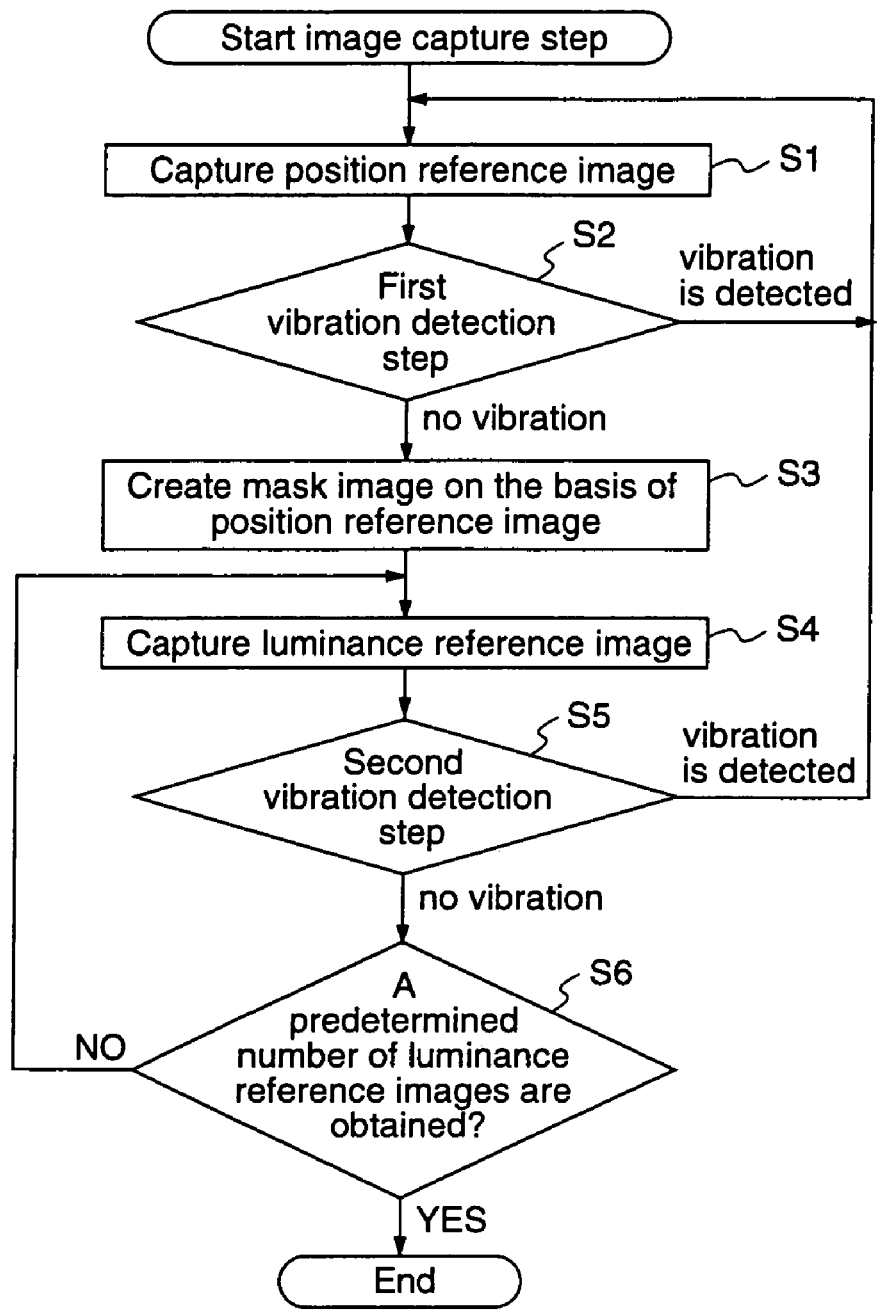
FIG. 2 is a diagram illustrating a flow chart of image capture steps according to a first embodiment of the present invention.

FIG. 2 is a flow chart illustrating a series of flows for the image capture steps performed by the gene expression analyzer according to the first embodiment.

Initially, in step S1, a position reference image for obtaining positions where the plurality of beads as imaging targets are present is captured into the CPU 120 in the apparatus 100. To be specific, the controller 121 in the CPU 120 initially controls the well plate driving unit 103 so as to move the well plate 101 so that the well 102 into which the observation targets have been injected is positioned right above the objective lens 105. Then, the controller 121 lights the LED 106 so as to apply the LED light to the well 102. The LED light becomes silhouette lights of the beads as observation targets in the well 102, and the silhouette lights are enlarged by the objective lens 105, and pass through the dichroic mirror 107 and the bandpass filter 108, and further are collected by the imaging lens 109, and reach the CCD camera 110. The controller 121 instructs the Z axis driving unit 112 to align the objective lens 105 with the focus position to image the silhouette lights, and thereafter instructs the CCD camera controller 111 to make the CCD camera 110 image the silhouette image of the plurality of beads. Then, the analysis unit 122 in the CPU 120 binarizes the imaged silhouette image. The binarized image is stored in the CPU 120 as the position reference image for obtaining positions where the respective imaging targets are present.

Figure 3A:
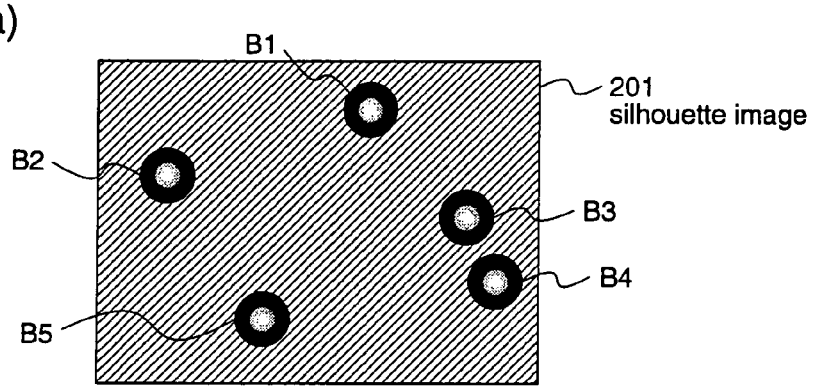
FIG. 3(a) shows a silhouette image.
Figure 3B:
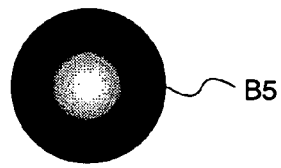
FIG. 3(b) is an enlarged view of a bead shown in FIG. 3(a)
Figure 3C:
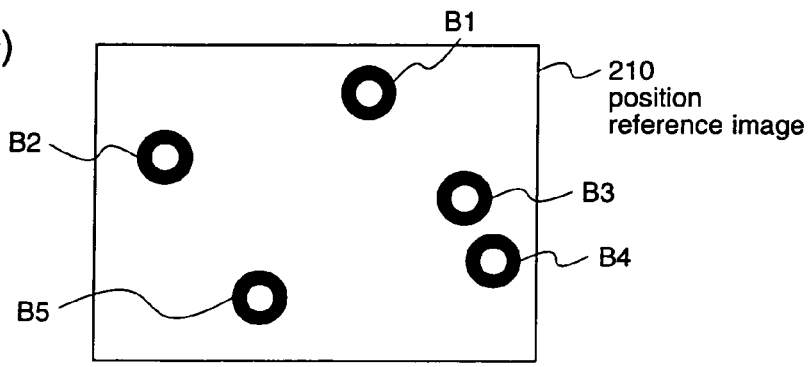
FIG. 3(c) shows a position reference image.

FIG. 3(a) is a diagram illustrating an imaged silhouette image, FIG. 3(b) is an enlarged view of a bead which is present in the silhouette image shown in FIG. 3(a), and FIG. 3(c) is a diagram illustrating a position reference image obtained on the basis of the silhouette image shown in FIG. 3(a). Then, while some hundreds of beads appear on an actual silhouette image, FIG. 3 shows only five pieces of beads for simplicity.

As shown in FIG. 3(b) a bead has a much lighter area at its center. This is because the bead is made of translucent acryl and the bead functions as a lens in the case of the LED light being applied, and the light is focused on the center part, and the center part becomes very light while the periphery of the bead becomes very dark since the light is bent and does not reach the periphery.

Next, in step S2, the first vibration detection unit 124 in the CPU 120 detects whether or not a vibration occurred when the position reference image imaging unit 130 imaged a silhouette image.

Figure 6:
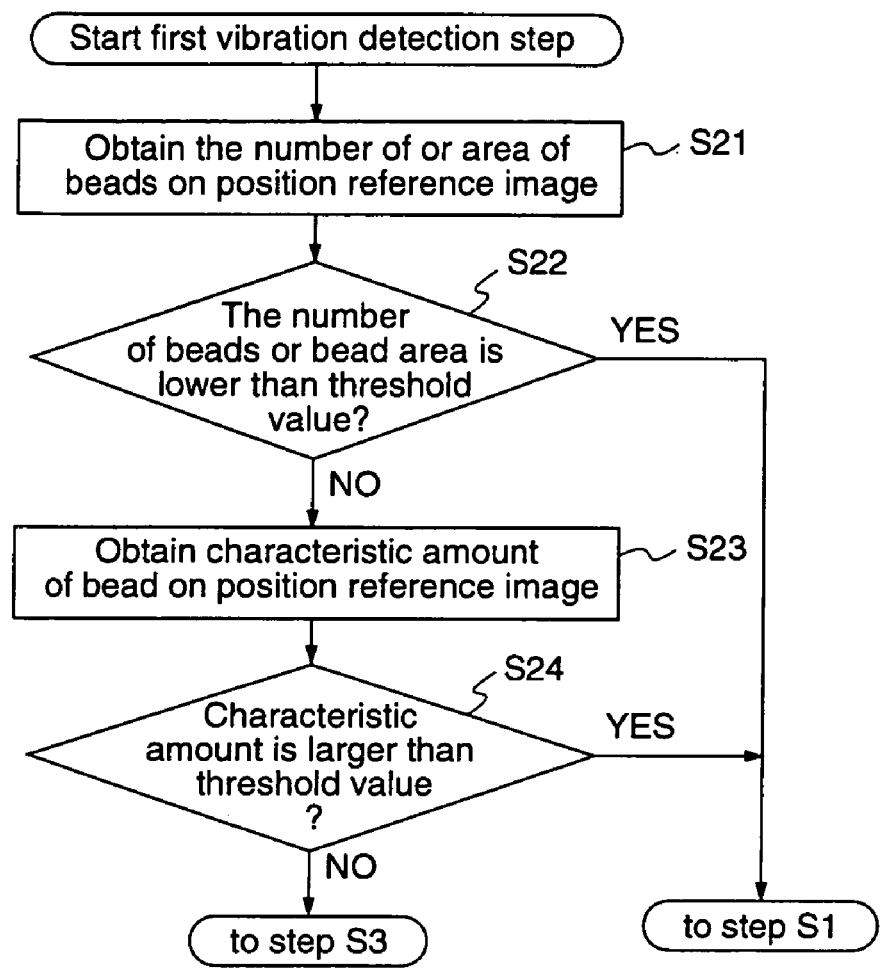
FIG. 6 is a diagram illustrating a flow chart of a first vibration detection steps according to the first embodiment of the present invention.

Hereinafter, a vibration detection method performed by the first vibration detection unit 124 will be described. FIG. 6 is a flow chart illustrating a flow of the first vibration detection steps.

In step S21, the number and area change detection unit 124*a* in the first vibration detection unit 124 initially detects the number of beads or each bead area on the position reference image, and in step S22 compares the number of beads or each bead area which is detected with a previously held threshold value.

Then, in a case where it is judged in the step S22 that the number of beads or each bead area is less than the threshold value, it is judged that a strong vibration occurred when the silhouette image was imaged, and the step shifts to step S1 shown in FIG. 2, and a silhouette image is re-imaged again.

Here, why the vibration can be detected by detecting the number of beads or each bead area appearing on the position reference image will be described.

Figure 4A:
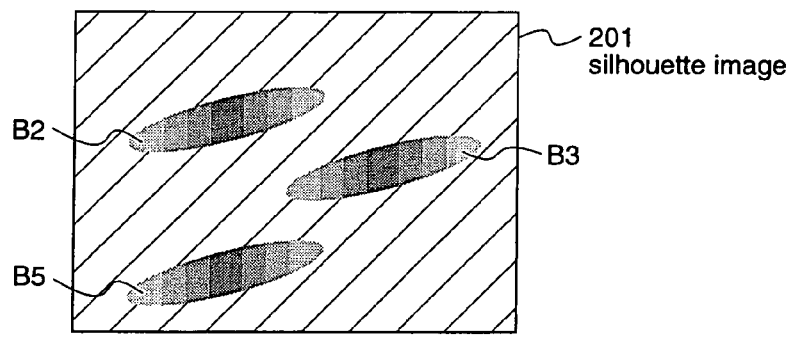
FIG. 4(a) shows a silhouette image.
Figure 4B:
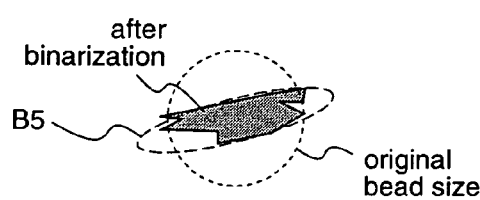
FIG. 4(b) is a diagram showing that one of the beads shown in FIG. 4(a) is binarized.

FIG. 4(*a*) is a diagram illustrating a silhouette image obtained in a case where a strong vibration occurred when the silhouette image was imaged, and FIG. 4(*b*) is a diagram showing that the bead B5 shown in FIG. 4(*a*) is binarized.

A silhouette image 201 imaged when the strong vibration occurred during imaging substantially blurs as shown in FIG. 4(*a*), and as a result, the number of beads are substantially reduced (the number is reduced from 5 to 3 in FIG. 4), or each area of the bead parts is reduced as shown in FIG. 4(*b*).

By utilizing this phenomenon, the number and area change detection unit 124*a* detects the number of beads and each bead area on the position reference image, and compares the number of beads or each bead area with a predetermined threshold value, thereby detecting whether or not a strong vibration occurred during imaging.

Next, a method for calculating a threshold value to be previously held in the number and area change detection unit 124*a* will be described.

The number N of beads to be injected into a well 102 is previously set, and the beads are uniformly distributed in the well 102. Accordingly, when the well area in the well 102 is $S_W$ and the well area on the position reference image is $S_M$, the number Nx of beads on the position reference image is obtained as $Nx=(S_W/S_M) \times N$ and a value having this as an upper limit is set as a threshold value for the number of beads. As this threshold value is closer to the upper limit value, the smaller vibration can be detected.

On the other hand, since each bead has the same shape, each bead area is calculated on the basis of the threshold value for the number of beads and the calculated area is set as a threshold value for the bead area. For example, the threshold value for the number of beads and the threshold value for each bead area on the position reference image 201 are set to 200 pieces and 80 pixels, respectively.

These threshold values are previously held, and in a case where the number of beads on the position reference image 201, which is detected by the number and area change detection unit 124*a*, is less than 200 pieces, it is judged that a strong vibration occurred during imaging. Otherwise, in a case where a bead area having the largest area of the respective bead areas on the position reference image 201, which is detected by the number and area change detection unit 124*a*, is less than 80 pixels, it is judged that a strong vibration occurred during imaging. Of course, all the bead areas on the position reference image 201 are calculated on the basis of the threshold value for the number of beads and the threshold value for each bead area, and the calculated value may be held as a threshold value for the bead area. In this case, when the bead area detected by the number and area change detection unit 124*a* is less than 200 pieces×80 pixels=16000 pixels, it is judged that a strong vibration occurred.

On the other hand, in a case where it is judged in the step S22 that the value detected by the number and area change detection unit 124*a* is equal to or larger than the threshold value, the shape change detection unit 124*b* in the first vibration detection unit 124 subsequently detects a characteristic amount of a bead which is present on the position reference image in step S23, and compares the characteristic amount with the threshold value which is previously held in the shape change detection unit 124*b* in step S24.

Then, when it is judged in the step S24 that the characteristic amount of the bead is larger than the threshold value, it is judged that a gentle vibration occurred while the silhouette image was imaged, and the step shifts to step S1 shown in FIG. 2, and a silhouette image is re-imaged again.

Figure 5A:
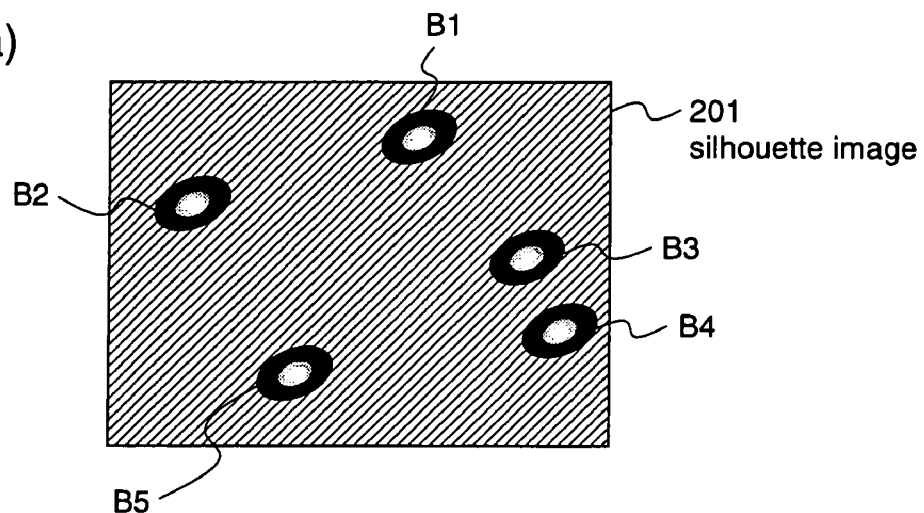
FIG. 5(a) shows a silhouette image.
Figure 5B:
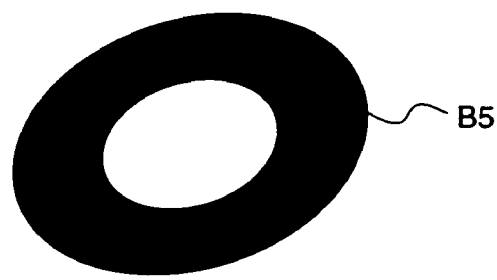
FIG. 5(b) is a diagram showing that one of the beads shown in FIG. 5(a) is binzrized.

FIG. 5(*a*) is a diagram illustrating a silhouette image obtained when a gentle vibration occurred during imaging, FIG. 5(*b*) is an enlarged view of a bead B5 present on the position reference image, which is obtained by binarizing the bead B5 shown in FIG. 5(*a*), and FIG. 5(*c*) is a diagram illustrating a part having a higher luminance which is present at the center part of the bead B5.

While the bead which is present in the silhouette image imaged when a gentle vibration occurred during imaging has its shape distorted a little and becomes elliptical as shown in FIG. 5(*a*), the number of beads remains unchanged and each bead area changes just a little, and thereby the vibration detection method performed by the number and area change detection unit 124*a* described above cannot be applied.

However, in a case where a gentle vibration occurred, the bead in the silhouette image has its shape distorted as described above, and therefore the shape change detection unit 124*b* utilizes this phenomenon to detect a change in bead shape and detects whether or not a gentle vibration occurred during imaging.

Hereinafter, a method for detecting a change in bead shape performed by the shape change detection unit 124*b* will be described.

The shape change detection unit 124*b* obtains a change in shape of the bead which is present on the position reference image by detecting whether or not the shape of the bead is elliptical. Accordingly, the largest bead diameter is detected as a value indicating a shape of the bead on the position reference image (hereinafter, referred to as "characteristic amount"), and when the largest diameter is larger than the previously held threshold value, it is judged that the vibration occurred.

Then, as shown in FIG. 5(*b*), in a case where the bead has a higher light transmittancy, the light is focused on the center part of the bead which functions as a lens and the center part has a much higher luminance value and keeps a stable shape also after binarized, and therefore the largest diameter of the shape of this part having the higher luminance is set as the characteristic amount.

Then, a value whose lower limit is a diameter of a bead in a normal state is set as the previously held threshold value. As the threshold value is closer to the lower limit, the smaller vibration can be detected. Then, the judgement as to whether the shape is elliptical or not can be also made in a method in which a length of the major axis and a length of the minor axis of the bead are obtained and in a case where the ratio therebetween is other than 1, the bead shape is judged as ellipse.

Hereinafter, a method for obtaining a characteristic amount in the case of the bead having a higher light transmittancy will be described.

Figure 5C:
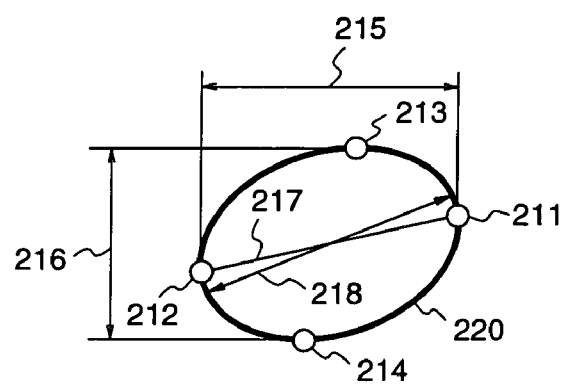
FIG. 5(c) is a diagram illustrating only a higher luminance portion of the bead shown in FIG. 5(b).

In FIG. 5c, the reference numeral 220 indicates a shape of a white area in a part of a bead, which has the higher luminance. For the shape 220, a coordinate of the rightmost pixel 211 is (Xmax, Ya), a coordinate of the leftmost pixel 212 is (Xmin, Yb), a coordinate of the uppermost pixel 213 is (Xa, Ymax), and a coordinate of the lowermost pixel 214 is (Xb, Ymin).

At this time, a width 215 is obtained as (Xmax−Xmin), and the height 216 is obtained as (Ymax−Ymin). In order to obtain a major axis of the ellipse, the width (Xmax−Xmin) is compared with the height (Ymax−Ymin), and when the width (Xmax−Xmin) is larger, $L=(Xmax-Xmin)^2+(Ya-Yb)^2$, while when the height (Ymax−Ymin) is larger, $L=(Xa-Xb)^2+(Ymax-Ymin)^2$.

The value of L obtained here is the square of the length 217 and is close to the square of the major axis 218 of the ellipse.

Then, the value of L is used only for comparison as to magnitude, and there is no need to obtain the square root thereof and the value L is used as it is.

The values of Ls of all the beads which are present on the position reference image are obtained as described above and thereafter an average value thereof is obtained as a value of LA.

At this time, a threshold value to be previously held in the shape change detection unit 124b is a value Lmax whose lower limit is the average value LA of the diameters of all the beads which are present on the position reference image in the case of no vibration having occurred.

On the other hand, in a case where no change in bead shape is detected by the shape change detection unit 124b in the step S24, it is judged that no vibration occurred and the step proceeds to the next step S3 shown in FIG. 2.

In step S3, a mask image is created on the basis of the position reference image.

Figure 7A:
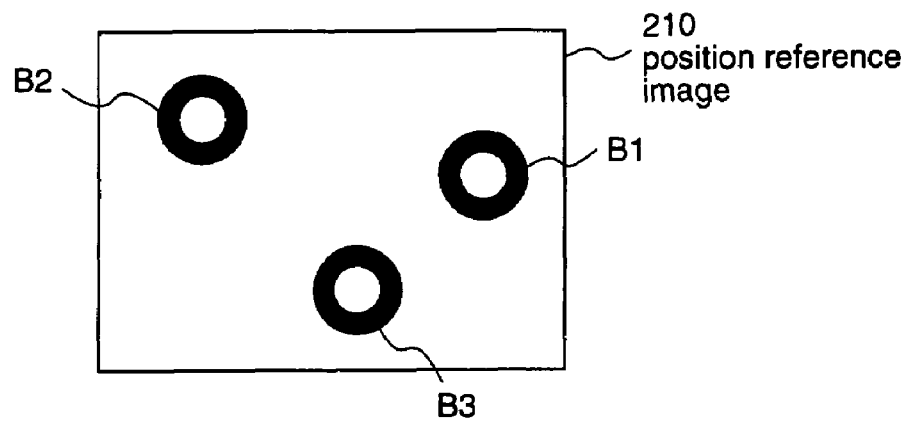
FIG. 7(a) shows a position reference image.
Figure 7B:
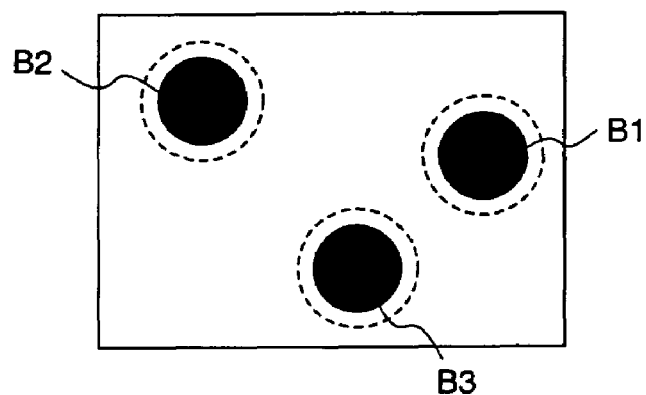
FIG. 7(b) is a diagram illustrating an intermediate process of creating the mask image.
Figure 7C:
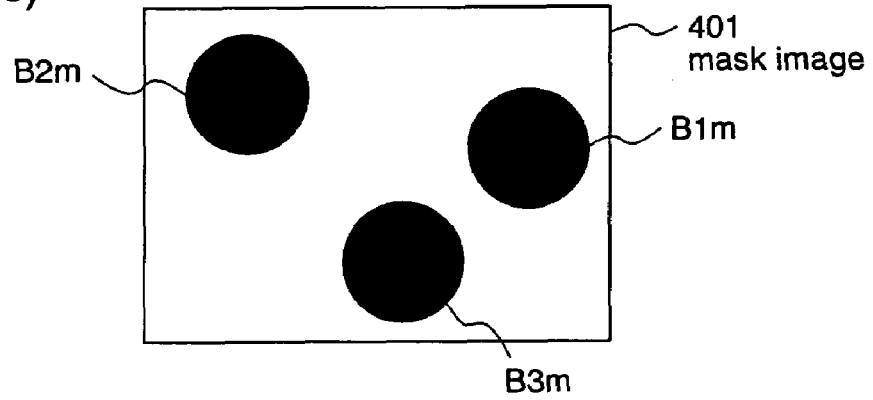
FIG. 7(c) shows the mask image obtained on the basis of the image shown in FIG. 7(a).

Hereinafter, a mask image will be described. FIG. 7(a) is a diagram illustrating a position reference image, FIG. 7(b) is a diagram illustrating an intermediate process of creating a mask image on the basis of the image shown in FIG. 7(a), and FIG. 7(c) is a diagram illustrating the created mask image.

The mask image indicates presence positions of beads which are present on the position reference image and is obtained by making the position reference image shown in FIG. 7(a). To be specific, as shown in FIG. 7(b), the center parts of the beads having the higher luminances are initially masked and thereafter the processing is performed so that the outer circumferences of the respective beads B1, B2 and B3 become slightly larger, thereby obtaining the mask image as shown in FIG. 7(c). Then, in the first embodiment, the processing is performed so that the outer circumference of each of the beads B1, B2 and B3 becomes one pixel larger.

Figure 8:
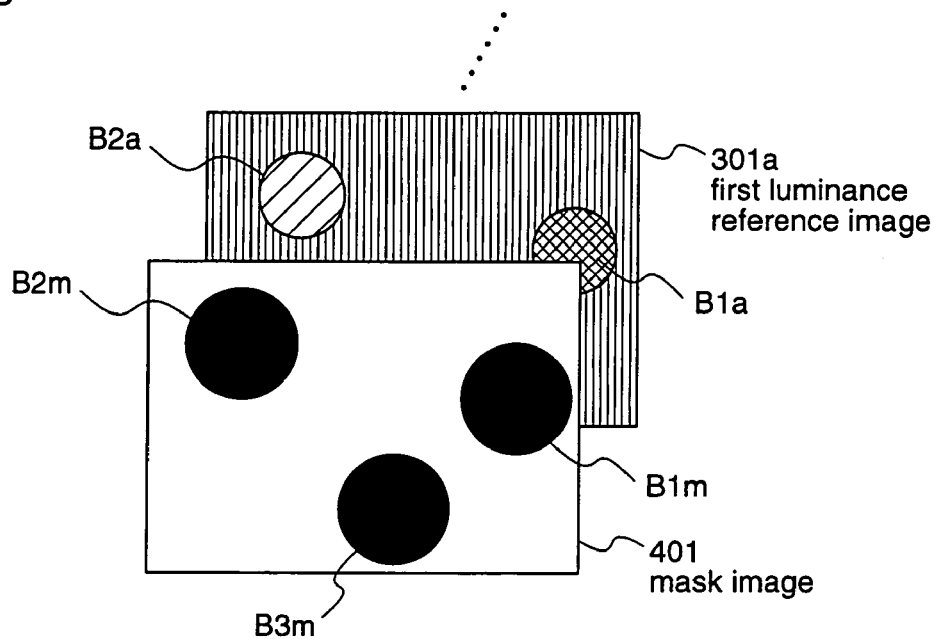
FIG. 8 is a diagram illustrating a mask image and a plurality of luminance reference images according to the first embodiment of the present invention.

Then, in step S4, a plurality of luminance reference images for obtaining the respective average luminance values of the imaging targets which have already passed through the respective optical filters are captured into the CPU 120. To be specific, the controller 121 in the CPU 120 initially has the LED 106 unlighted and makes the excitation light source 113 apply an excitation light. The dichroic mirror 107 reflects the excitation light in the direction of the objective lens 105. The objective lens 105 focuses the light from the dichromic mirror 107 on a plurality of beads as the observation targets in the well 102. The plurality of beads which are present in the well 102 indicate light emission patterns corresponding to the spectral characteristics by the light which is applied from the objective lens 105, respectively, and the lights emitted from the respective beads pass through the objective lens 105, the dichroic mirror 107 and the bandpass filter 108, and further are collected by the imaging lens 109, and reach the CCD camera 110 as described for the bead silhouette lights obtained by applying the LED light to the beads. At this time, since the bandpass filter 108 has the characteristic that it passes only a specific wavelength band, only the light of the specific wavelength band emitted from the beads reach the CCD camera 110. In this state, the controller 121 instructs the CCD camera controller 111 to make the CCD camera 110 image a luminance image of only the specific wavelength band which passes through the bandpass filter 108 among the lights emitted from the beads. Then, the analysis unit 122 in the CPU 120 binarizes the imaged luminance image and the binarized image is stored as a luminance reference image in the CPU 120. FIG. 8 is a diagram illustrating the mask image and the luminance reference image.

A luminance reference image is captured into the CPU 120 in the step S4, and thereafter in step S5 the second vibration detection unit 125 detects whether or not a vibration occurred when the luminance image to be captured was imaged using the mask image created in the step S3.

Hereinafter, a vibration detection method for the luminance reference image performed by the second vibration detection unit 125 will be described.

When a vibration is detected for the luminance reference image, the position reference image 210 imaged with no vibration occurring has been already stored in the CPU 120 and the mask image 401 indicating the bead presence positions in the image has been created on the basis of the position reference image.

As described above, the outer circumferences of the bead areas B1m, B2m, and B3m on the mask image 401 are slightly larger than the outer circumferences of the beads B1, B2 and B3 which are present on the position reference image, respectively.

Figure 9A:
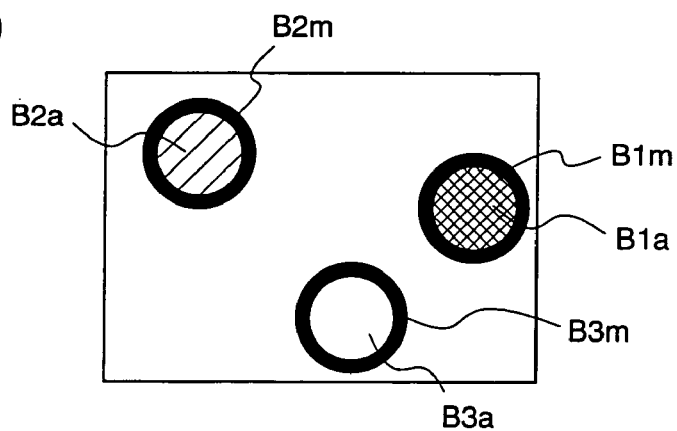
FIG. 9(a) is a diagram showing that the mask image is overlaid on the luminance reference image in a case where no vibration occurred.

Here, since the processing is performed so that each of the outer circumferences of the bead areas B1m, B2m, and B3m is one pixel larger than each of the outer circumferences of the beads B1, B2 and B3, when no vibration occurred when the luminance image was imaged, in a case where the mask image 401 is overlay-displayed on the luminance reference image 301, the masked bead areas B1m, B2m and B3m on the mask image 401 should be present around the outer circumferences of the bead areas B1a to B3a on the luminance reference image 301a, respectively, as shown in FIG. 9(a).

Figure 9B:
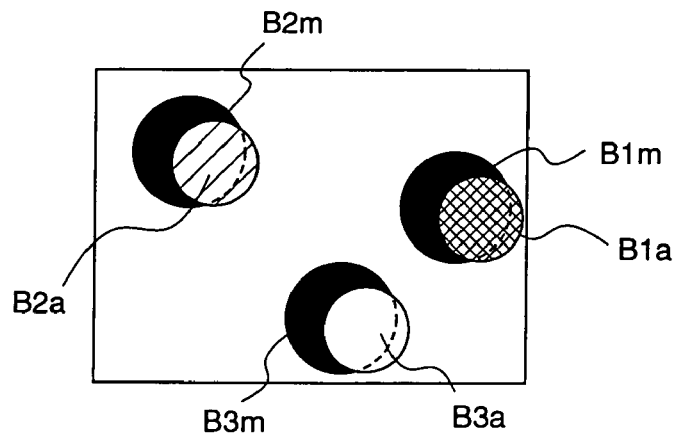
FIG. 9(b) is a diagram showing that the mask image is overlaid on the luminance reference image in a case where a vibration occurred.

FIG. 9 is a diagram illustrating a relationship between the bead areas on the mask image and the bead areas on the first luminance reference image, wherein FIG. 9(a) shows that the mask image is overlay-displayed on the luminance reference image in a case where no vibration occurred while FIG. 9(b) shows that the mask image is overlay-displayed on the luminance reference image in a case where a vibration occurred before or during imaging.

In FIG. 9, regions B1a, B2a, and B3a are regions that are displayed by an emission from the bead B1, B2, and B3 by irradiating an excitation light to the beads B1, B2, and B3, respectively. Regions B1m, B2m, and B3m are regions displayed by overlay-displaying the mask area of the beads B1, B2, and B3 on the luminance reference image, respectively.

In a case where no vibration occurred before or when the luminance reference image was imaged, since no deviation in bead position between the position reference image and the luminance reference image is generated, the respective bead areas B1a, B2a, and B3a on the luminance reference image 301a are located inside the respective bead areas B1m, B2m, and B3m which are obtained by overlay-displaying the mask image on the luminance reference image as shown in FIG. 9(a). Accordingly, in this case, no part having a higher luminance is present outside the bead areas B1m, B2m and B3m which are obtained by overlay-displaying the mask image on the luminance reference image 301a.

On the other hand, when a vibration occurred before or when the luminance reference image was imaged, deviations in the bead positions between the position reference image and the luminance reference image are generated, the respective bead areas B1a, B2a, and B3a on the luminance reference image 301a extrudes outside the respective bead areas B1m, B2m, and B3m which are obtained by overlay-displaying the mask image on the luminance reference image 301a as shown in FIG. 9(b). Accordingly, in this case, parts having the higher luminances are present outside the bead areas B1m, B2m and B3m which are obtained by overlay-displaying the mask image on the luminance reference image 301a.

Figure 10:
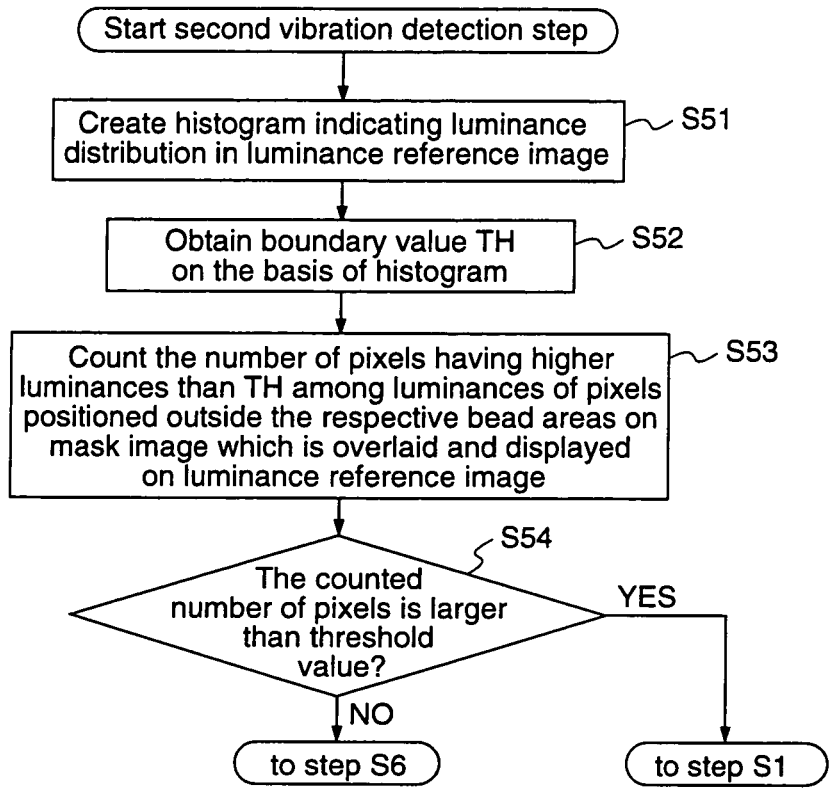
FIG. 10 is a diagram illustrating a flow chart of a second vibration detection steps according to the first embodiment of the present invention.

The second vibration detection unit 125 utilizes the above described phenomenon to detect a vibration for the luminance reference image. FIG. 10 is a flow chart illustrating a flow of the second vibration detection steps.

Initially, in step S51, the luminance distribution in the first luminance reference image 301a is checked. In the luminance reference image 301a of the first embodiment, the background part which occupies a larger part of the whole area indicates a lower luminance while only the excited areas B1a, B2a and B3a where the beads are present indicate higher luminances.

Accordingly, in order to check the luminance distribution in the luminance reference image, for each gradation, the number of pixels indicating the gradation is obtained on the basis of the luminance reference image 301a to create a histogram. FIG. 11 shows a histogram created on the basis of the luminance reference image.

Then, in step S52, the histogram created in the step S51 is searched from the low luminance side to obtain a luminance value IL at which the number of pixels positioned on the low luminance side totals to 5% of all the pixels, and further, the histogram is searched from the high luminance side to obtain a luminance value IH at which the number of pixels positioned on the high luminance side totals to 0.5% of all the pixels. Here, the ratio of the total number of pixels is different between the low luminance side and the high luminance side because the distribution on the low luminance side is dense while the distribution on the high luminance side is thin.

Then, the luminance values IL and IH obtained as described above are substituted into the (formula 1) shown as below to obtain a boundary value TH.

Boundary value $TH=(IL+IH)/2$ (formula 1)

Then, in step S53, the whole luminance reference image 301a is searched to count the number of pixels having the higher luminances than the boundary value TH obtained as described above among the pixels positioned outside the bead areas B1m, B2m, and B3m in the mask image overlay-displayed.

In step S54, the number of pixels having the higher luminance than the boundary value TH obtained in the step S53 is compared with a threshold value previously held in the second vibration detection unit 125, and in a case where the number of pixels having the higher luminance than the boundary value TH is larger than the threshold value, it is judged that a vibration occurred during imaging, and the step shifts to step S1 shown in the FIG. 2, and the position reference image is also re-imaged again.

Then, in this case, the total number of pixels positioned outside the bead areas B1m, B2m, and B3m in the mask image which is overlay-displayed on the luminance reference image 301a is obtained, and in a case where a ratio of the number of pixels having the higher luminance than the boundary value TH obtained in the step S53 to the total number of pixels exceeds a predetermined ratio, it may be judged that a vibration occurred.

Further, while all the pixels positioned outside the bead areas B1m, B2m, and B3m in the mask image which is overlay-displayed on the luminance reference image 301a are searched in the above described method, in a case where the expected vibration is not so strong and the amount of deviation of the beads due to the vibration is approximately lower than a diameter of the bead, it can be detected whether or not the vibration occurred by searching only the pixels close to the outer circumferences of the bead areas B1m, B2m, and B3m in the mask image which is overlay-displayed on the luminance reference image for shortening processing time.

That is, the luminances of the pixels bordering the outer circumferences of the respective bead areas B1m, B2m, and B3m in the mask image which is overlay-displayed on the luminance reference image are checked to count the number of pixels indicating the higher luminances than the boundary value TH. Then, in a case where the total number of pixels counted, or a ratio of the total number of pixels counted to the total number of pixels whose luminances are checked is larger than a predetermined threshold value, it may be judged that a vibration occurred.

On the other hand, in a case where it is judged in the step S54 that the number of pixels having the higher luminances than the boundary value TH obtained in the step S53 is equal to or lower than the threshold value, it is judged that no vibration occurred, and the step shifts to the next step S6 shown in FIG. 2.

In step S6, it is judged whether or not a predetermined number of luminance reference images are captured into the CPU 120, and in a case where the predetermined numbers have not been captured yet, the step shifts to the step S4 shown in FIG. 2, and the next luminance image is imaged and it is detected whether or not a vibration occurred before or when the luminance image was imaged using the mask image 401.

On the other hand, in a case where it is judged in the step S6 that the predetermined number of luminance reference images are captured, the image capture step is completed.

As described above, in the first embodiment, the CPU 120 contains a first vibration detection unit 124 which detects whether or not a vibration occurred when the position reference image imaging unit 130 imaged a silhouette image, and a second vibration detection unit 125 which detects whether or not a vibration occurred when the luminance reference image imaging unit 140 imaged a luminance image. The first vibration detection unit 124 uses the imaged position reference image to detect whether or not a vibration occurred in imaging, and further the second vibration detection unit 125 uses a mask image indicating bead presence positions which is created on the basis of the position reference image for which no vibration is detected to detect whether or not a vibration occurred in imaging every time a luminance reference image is imaged. In a case where the respective vibration detection units 124 and 125 detect vibrations, all the images are re-imaged, and thereby images imaged when the vibration occurred can be securely and easily eliminated, thereby enabling the apparatus to make data analysis with substantially high reliability.

Then, while in the first embodiment the background portion of the luminance reference image has a lower luminance and the areas in which beads are excited have higher luminances, even when the relation of the luminnaces is reverse, the vibration can be detected in a like manner.

[Embodiment 2]

In the first embodiment, when a vibration is detected for the luminance reference image even after some luminance reference images among a predetermined number of luminance reference images are obtained, all the images are re-obtained. On the other hand, in the second embodiment, when the vibration is detected for the luminance reference image after some luminance reference images among a predetermined number of luminance reference images are obtained, not all the images are not re-obtained, but images imaged before the vibration is detected are held as they are, the position reference image which is used for obtaining luminance values of the luminance reference image for which the vibration is detected is obtained and the luminance reference image for which the vibration is detected is re-imaged again.

The vibration detection method according to the second embodiment is applied to a case where an amount of deviation of the bead is lower than the diameter of the bead when the mask image is overlay-displayed on the luminance reference image. Accordingly, it is assumed that mechanical countermeasures are taken for the imaging apparatus according to the second embodiment and thereby the vibration during imaging is substantially reduced.

In the second embodiment, a gene expression analyzer which has the constituents similar to those described for the first embodiment, and analyzes the spectral characteristics of the beads which are present in the imaged image to identify the kinds of the beads and identifies mRNAs corresponding to the kinds of the beads is taken as an example of an imaging apparatus. Further the imaging targets are beads having various spectral characteristics, each of which has a diameter of about 10 μm.

Hereinafter, an operation will be described.

The gene expression analyzer of the second embodiment images beads as observation targets and captures a position reference image and a plurality of luminance reference images and thereafter analyzes the spectral characteristics of the beads using the captured images as described for the prior art apparatus 600. (refer to FIG. 14)

The process of analysis steps according to the second embodiment is the same as the process of analysis steps for the prior art apparatus, and therefore the process of image capture steps of capturing images will be described in detail here.

Figure 12:
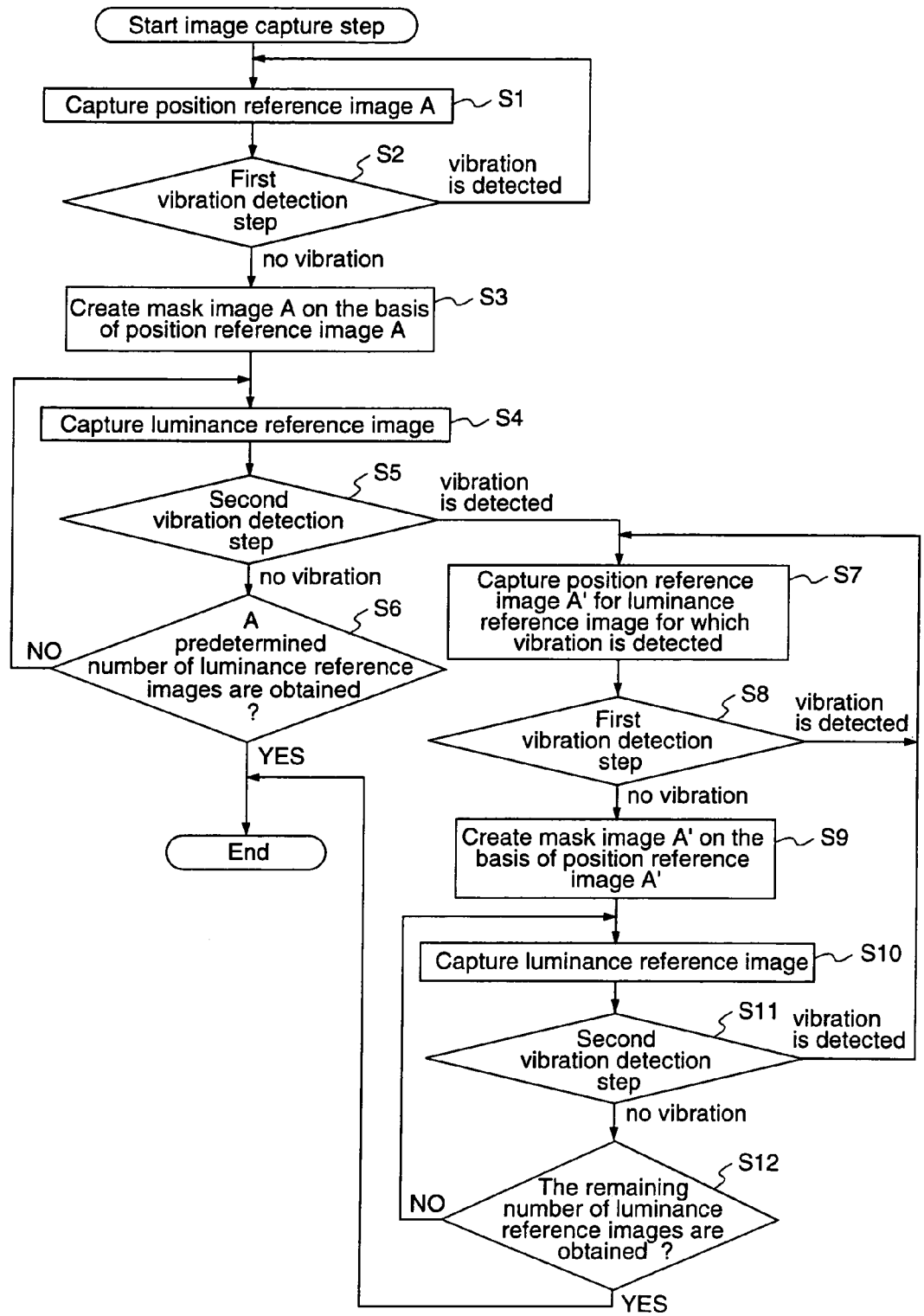
FIG. 12 is a diagram illustrating a flow chart of the image capturing steps according to a second embodiment of the present invention.
Figure 13:
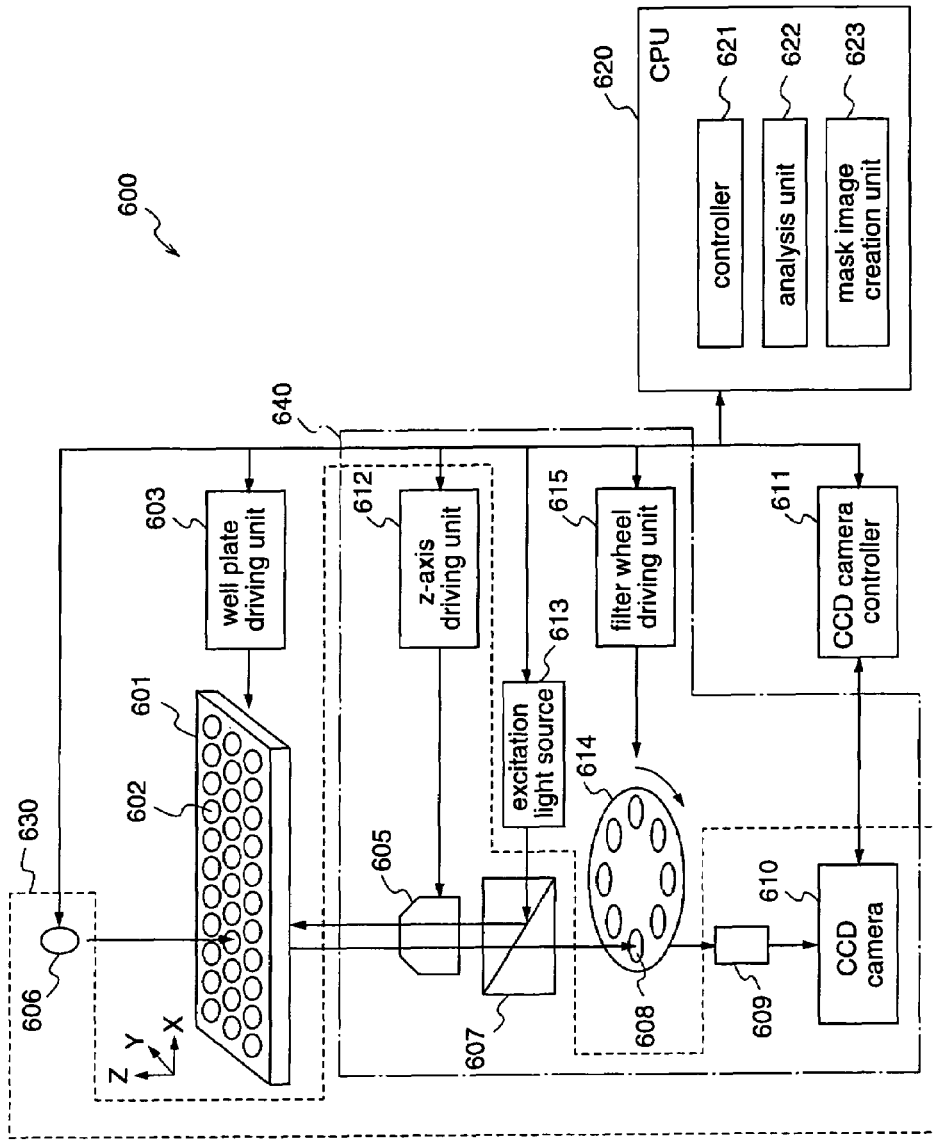
FIG. 13 is a diagram illustrating a construction of a prior art gene expression analyzer using a fluorescence microscope.

FIG. 12 is a flow chart illustrating a series of flows of the image capture steps of the gene expression analyzer according to the second embodiment.

Initially, in step S1, a position reference image for obtaining positions where a plurality of beads as imaging targets are present is captured into the CPU 120 in the apparatus 100. To be specific, the controller 121 in the CPU 120 initially controls the well plate driving unit 103 so as to move the well plate 101 so that the well 102 into which the observation targets have been injected is positioned right above the objective lens 105. Then, the LED 106 is lighted and silhouette lights of the plurality of beads as observation targets in the well 102 pass through the objective lens 105, the dichroic mirror 107, the bandpass filter 108, and the imaging lens 109, and the CCD camera 110 images a silhouette image. Then, the position reference image A obtained by binarizing the silhouette image by the analysis unit 122 in the CPU 120 is stored in the CPU 120.

Next, in step S2, the first vibration detection unit 124 detects whether or not a vibration occurred when the position reference image imaging unit 130 imaged the silhouette image with using the same method as that described for the first embodiment with reference to FIG. 6. Then, while in the first embodiment the number and area change detection unit 124a detects a strong vibration on the basis of the change in the number of beads or the respective bead areas, which beads are present on the position reference image, and thereafter the shape change detection unit 124b detects change in bead shape to detect a gentle vibration, only the shape change detection unit 124b may detect the vibration which occurred when the image was imaged in the second embodiment since it is assumed that the vibration is substantially reduced.

Then, in a case where a vibration is detected in the step S2, the step shifts to the step S1, and the position reference image A is re-obtained again.

On the other hand, in a case where no vibration is detected in the step S2, the step shifts to the next step S3 and a mask image A indicating bead presence positions on the image is created on the basis of the position reference image A in the same method as described for the first embodiment.

Thereinafter, in step S4, the first luminance reference image is captured. Then, in step S5, the second vibration detection unit 125 detects a vibration for the luminance reference image obtained in the step S4 using the mask image A created in the step S3 in the same method as described for the first embodiment.

In a case where no vibration is detected in the step S5, the step shifts to the next step S6, and it is judged whether or not a predetermined number of luminance reference images are captured into the CPU 120, and in a case where the predetermined number of luminance reference images have not been captured yet, the step shifts to the step S4, and the steps S4 to S6 are repeated until the predetermined number of luminance reference images can be obtained.

Here, for example, it is assumed that a vibration is detected in the step S5 after the sixth luminance reference image is captured into the CPU 120. In this case, the step shifts to step S7, and the position reference image A' for the luminance reference image for which the vibration is detected is obtained again.

Then, in step S8, the first vibration detection unit 124 detects whether or not a vibration occurred when the image was imaged using the position reference image A' in the same method as performed in the step S2.

In a case where no vibration is detected in the step S8, the step shifts to the next step S9, and a mask image A' is created on the basis of the position reference image A'.

On the other hand, in a case where a vibration is detected in the step S8, the step shifts to the step S7 and the position reference image A' is re-obtained again.

Next, in step S10, the sixth luminance reference image is captured again. Then, in step S11, the second vibration detection unit 125 detects a vibration for the sixth luminance reference image using the mask image A' created in the step S9 in the same method as described for the first embodiment. Then, in a case where no vibration is detected in the step S1, the step shifts to step S12, and it is judged whether the remaining luminance reference images are captured into the CPU 120 or not, and in a case where the remaining luminance reference images have not been captured yet, the steps S10 to S12 are repeated until all the remaining luminance reference images are obtained.

The images obtained in the method described above are the position reference image A, the position reference image A' and 8 pieces of luminance reference images, and the bead areas on the respective first to fifth luminance reference images are obtained on the basis of the bead areas on the mask image A, and the bead areas on the respective sixth to eighth luminance reference images are obtained on the basis of the bead areas on the mask image A'.

In the second embodiment, it is assumed that the amount of deviation of the bead due to the vibration is approximately lower than the diameter of the bead as described above, and therefore the correspondence relationship of the bead between the mask image A and the mask image A' can be easily obtained by utilizing the fact that the respective beads are overlapped.

Figure 16:
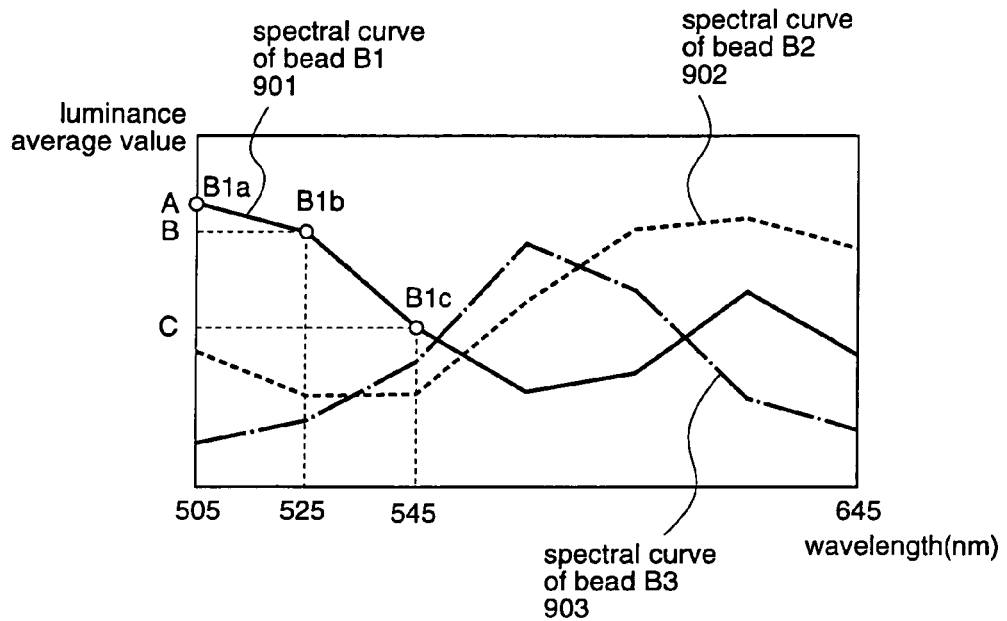
FIG. 16 is a diagram illustrating plotted luminance average values.
Figure 17A:
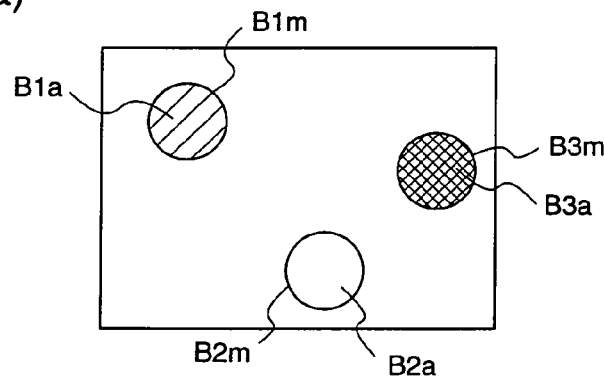
FIG. 17(a) is a diagram showing that the mask image is overlaid on the luminance reference image in a case where no vibration occurred.
Figure 17B:
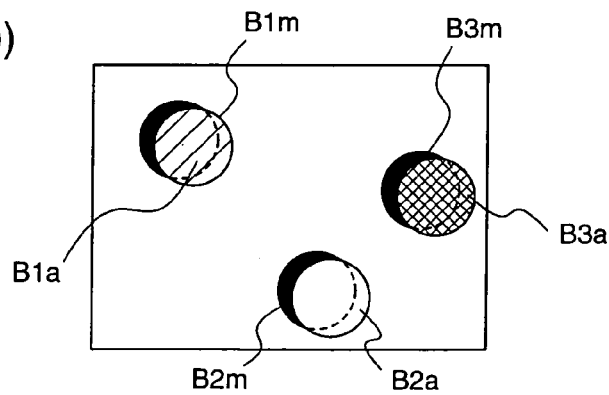
FIG. 17(b) is a diagram showing that the mask image is overlaid on the luminance reference image in a case where a vibration occurred.

Accordingly, in order to create the spectral distribution chart as shown in FIG. 16, the average of the luminances of each area on each of the first to fifth luminance reference images, which area corresponds to each bead area on the mask image A and the average of the luminances of each area on each of the sixth to eighth luminance reference images, which area corresponds to each bead area on the mask image A' being overlapped on each bead area on the mask image A may be obtained to plot all the luminance averages.

The spectral characteristics of the respective beads can be obtained on the basis of the spectral curve created as described above, thereby enabling the kinds of the beads to be identified according thereto.

Further, after the sixth luminance reference image is obtained as described above, for example, in a case where a vibration is detected for the seventh luminance reference image, the step shifts to step S7, and the position reference image A" for the seventh luminance reference image for which the vibration is detected is obtained again, and a mask image A" is created on the basis of the position reference image A". When the analysis is made, the position reference image A, the position reference image A', the position reference image A", and 8 pieces of luminance reference images are used, and each bead area on each of the first to fifth luminance reference images is obtained on the basis of each bead area on the mask image A, each bead area on the sixth luminance reference image is obtained on the basis of each bead-area on the mask image A', and each bead area on each of the seventh to eighth luminance reference images is obtained on the basis of each bead area on the mask image A". Further, in order to create the spectral distribution chart shown in FIG. 16, the respective luminance averages of the bead areas on the first to fifth luminance reference images, which areas correspond to the bead areas on the mask image A, the respective luminance averages of the bead areas on the sixth luminance reference image, which areas correspond to the bead areas on the mask image A' which overlap on the bead areas on the mask image A, and the respective luminance averages of the bead areas on the seventh to eighth luminance reference images, which areas correspond to the bead areas on the mask image A" which overlap on the bead areas on the mask image A' may be obtained to plot all the luminance averages.

As described above, in the second embodiment, the CPU 120 contains a first vibration detection unit 124 which detects whether or not a vibration occurred when the position reference image imaging unit 130 imaged a silhouette image and a second vibration detection unit 125 which detects whether or not a vibration occurred when the luminance reference image imaging unit 140 imaged luminance images. The position reference image A is imaged and thereafter the first vibration detection unit 124 detects whether or not a vibration occurred during imaging using the imaged position reference image A, and further the respective luminance reference images are imaged and thereafter the second vibration detection unit 125 detects whether or not a vibration occurred during imaging using a mask image A indicating bead presence positions on the image, which mask image A is created on the basis of the position reference image A for which no vibration is detected. In a case where a plurality of luminance reference images are already imaged, and then a vibration is detected for the luminance reference image which is subsequently imaged, a position reference image A' which is other than the position reference image A is obtained again, and it is detected whether or not a vibration occurred for the luminance reference image which is obtained again after the vibration is detected using the mask image A' created on the basis of the position reference image A', and therefore the image imaged with the vibration occurring can be eliminated, thereby enabling the apparatus to make data analysis with extremely high reliability. Further, the time for obtaining all the images can be shortened.

The imaging apparatus according to the present invention is useful as a bioanalyzer such as a gene expression analyzer using a fluorescence microscope, which observes the spectral characteristics using a plurality of filter images since reliable data analysis can be made by preventing the positions of the filter images from deviating from each other due to the influence of vibration.

What is claimed is:

1. An imaging apparatus comprising:
   a position reference image creation unit for applying reference light to plural imaging targets each having the same shape, and creating silhouettes of the imaging targets, thereby to obtain a position reference image utilized for obtaining positions at which the respective imaging targets are present;
   a luminance reference image creation unit for applying an excitation light to the imaging targets, and creating luminance images of the imaging targets for respective optical filters each having a predetermined passing wavelength band, thereby to obtain plural luminance reference images utilized for obtaining luminance of respective imaging targets for each optical filter;
   a first vibration detection unit for detecting at least one among a change amount of the number or the area and a shape change of the imaging targets on the position reference image, and judging whether vibrations have occurred in the respective imaging targets during imaging the imaging target by the position reference image creation unit on the basis of the detected result;
   a mask image creation unit for creating a mask image that shows areas where the imaging targets are present from the position reference image for which the first vibration detection unit has detected no vibrations; and
   a second vibration detection unit for overlay-displaying the mask image on the respective luminance reference images, detecting whether or not the imaging targets are present outside the existing areas of the respective imaging targets, and judging whether or not vibrations have occurred in the respective imaging targets during imaging the imaging target by the luminance reference image creation unit on the basis of the detected result.

2. The imaging apparatus as defined in claim 1, wherein the first vibration detection unit includes a shape change detection unit for obtaining a characteristic amount indicating a shape change of each imaging target in the position reference image, the characteristic amount detected by the first vibration detection unit is compared with a predetermined threshold value for the characteristic amount, and when among the plural imaging targets in the position reference image, there are present a predetermined number of or a predetermined rate of imaging targets that have the characteristic amounts larger than the threshold value, it is judged that vibrations have occurred.

3. The imaging apparatus as defined in claim 2, wherein the characteristic amount for the imaging target having a spherical shape is the largest diameter of the imaging target.

4. The imaging apparatus as defined in claim 2, wherein the characteristic amount for the imaging target that has a spherical shape and comprises a substance of a high light transparency is the largest diameter of a high luminance portion of the imaging target.

5. The imaging apparatus as defined in claim 1, wherein the mask image creation unit creates a mask image by pasting areas corresponding to the imaging targets and their outer circumference areas in the position reference image for which imaging target areas no vibrations are detected by the first vibration detection unit.

6. The imaging apparatus as defined in claim 1, wherein the second vibration detection unit overlay-displays the mask image on the luminance reference images, and compares the luminance values of the pixels that are located outside the existing areas of the imaging targets in the luminance reference image with a predetermined threshold value for the luminance value, and when among the pixels located outside the existing areas of the imaging targets, there are present a predetermined number of or a predetermined rate of pixels that have the luminance values larger than the threshold value, it is judged that vibrations have occurred.

7. The imaging apparatus as defined in claim 1, wherein the second vibration detection unit overlay-displays the mask image on the luminance reference images, and compares the luminance values of the pixels that are located close to the outer circumferences of the existing areas of the imaging targets in the luminance reference images with a predetermined threshold value for the luminance value, and when among the pixels that are located close to the circumferences of the existing areas of the imaging targets, there are present a predetermined number of or a predetermined rate of pixels having higher luminance values than the threshold value, it is judged that vibrations have occurred.

8. The imaging apparatus as defined in claim 1, wherein when vibrations are detected by either the first vibration detection unit or the second vibration detection unit, all of the position reference image and the respective luminance reference images are newly captured.

9. The imaging apparatus as defined in claim 1, wherein when vibrations are detected by either the first vibration detection unit or the second vibration detection unit, the luminance reference images for which vibrations are detected as well as the position reference image for obtaining the existing positions of the imaging targets on the luminance reference images for which vibrations are detected are newly captured.

* * * * *